United States Patent [19]

Bloomfield

[11] Patent Number: 4,592,727
[45] Date of Patent: Jun. 3, 1986

[54] PIEZOELECTRIC POLYMERIC FILM DISCRIMINATING BITE FORCE OCCLUSAL INDICATOR

[75] Inventor: Philip E. Bloomfield, Bala Cynwyd, Pa.

[73] Assignee: Pennwalt Corporation, Philadelphia, Pa.

[21] Appl. No.: 613,687

[22] Filed: May 24, 1984

[51] Int. Cl.4 .............................................. A61C 9/00
[52] U.S. Cl. ...................................... 433/71; 433/68; 128/777
[58] Field of Search .................... 433/71, 68; 128/777, 128/776, 774, 782

[56] References Cited

U.S. PATENT DOCUMENTS

| 3,349,489 | 10/1967 | Shackelford | 433/68 |
| 3,983,865 | 10/1976 | Shepard | 128/777 |
| 4,334,542 | 6/1982 | Takinishi et al. | 128/777 |
| 4,390,028 | 6/1983 | Okano et al. | 433/71 |
| 4,402,326 | 9/1983 | Okano et al. | 433/68 |
| 4,488,873 | 12/1984 | Bloomfield et al. | 433/71 |
| 4,521,186 | 6/1985 | Wodlinger et al. | 433/71 |

Primary Examiner—John J. Wilson

[57] ABSTRACT

Strips are prepared from a stack of two superposed metallized polymer films, each film having piezoelectric properties. The stack is coated with a conventional plastically deformable wax impression material to provide the normal visual indication of bite deflection and premature teeth engagement. The stack of metallized polymer films provides means through which sliding bite forces exerted during occlusal analysis may be monitored and recorded.

3 Claims, 8 Drawing Figures

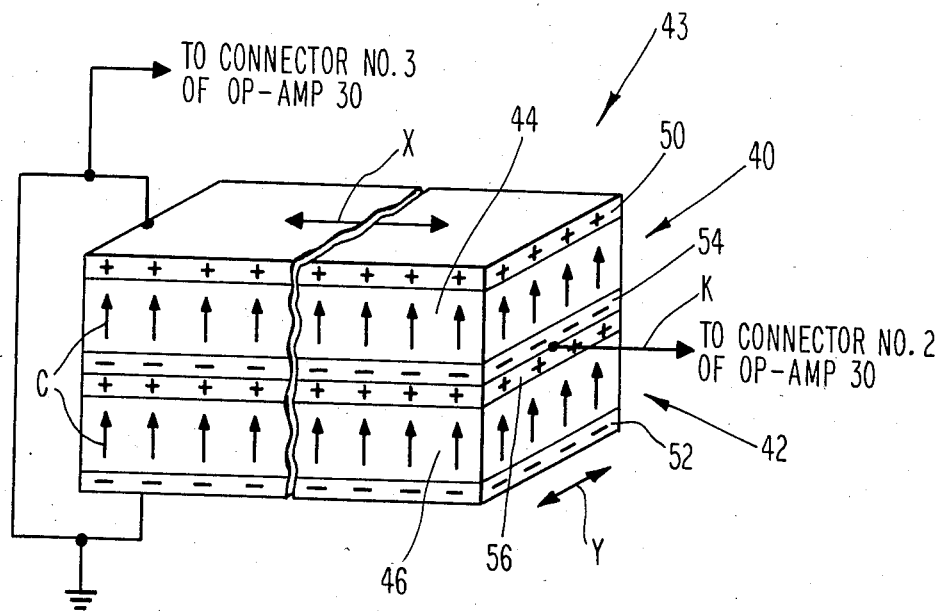
_Fig. 5_
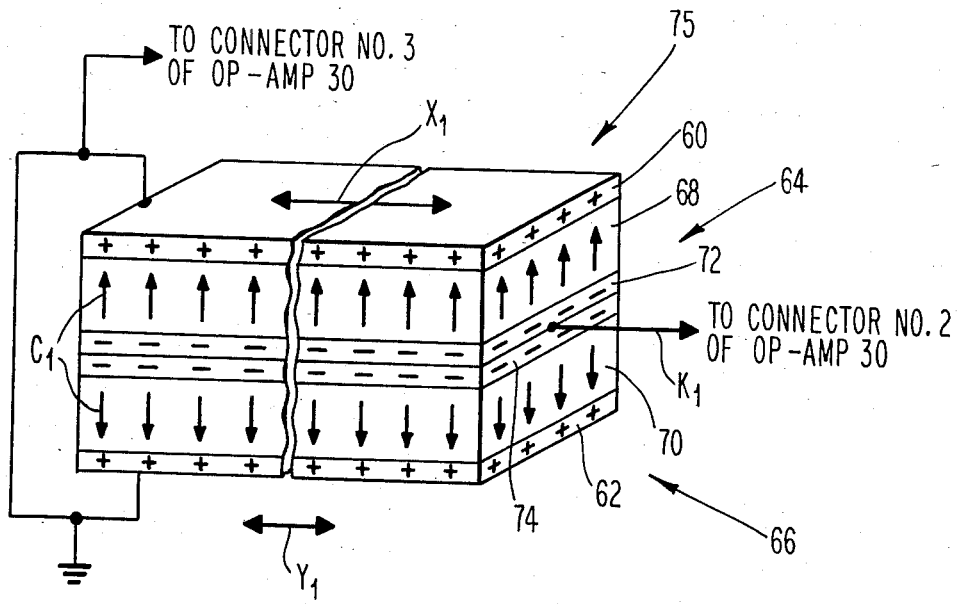
_Fig. 6_

PIEZOELECTRIC POLYMERIC FILM DISCRIMINATING BITE FORCE OCCLUSAL INDICATOR

CROSS-REFERENCE TO RELATED APPLICATIONS

Reference is hereby made to copending patent application of Philip E. Bloomfield et al for "Piezoelectric Polymeric Film Occlusal Force Indicator", Ser. No. 504,203, filed June 14, 1983, and now U.S. Pat. No. 4,488,873.

STATEMENT OF THE INVENTION

The present invention relates to dental devices and more particularly to such a device which includes a stack of two superposed transducing piezoelectric polymer films coated with conventional impression wax for providing bite impression data and sliding bite force data.

BACKGROUND AND SUMMARY OF THE INVENTION

Dental impression wafers, as disclosed in U.S. Pat. No. 3,604,116, having a sheet carrier of strong pliable material sandwiched between deformable impression material such as bite wax are known. The wafer permits a precise visual indication of premature engagement of the teeth and bite deflection. The wafer however does not permit measurement or monitoring of the bite force or force exerted on the wafer by the patient during occlusal analysis, or, more specifically, sliding bite force anaylsis, which analyses may suggest left/right muscular disbalance due possibly to premature contact or deflected contact between teeth of the maxilla and mandible. The force exerted during occlusal analyses can now be monitored, and permanent records of the force exerted on either side of the mouth are readily obtainable. These records may be used to later compare the patient's muscle activity before and after correction and adaptation.

Briefly, the invention comprises a stack of two superposed thin metallized films of polymer material having piezoelectric properties. The stack is coated on substantially all outer surfaces and edges with a conventional dental impression material, typically bite wax. The polymer film is preferably KYNAR ® piezofilm, a polyvinylidene fluoride product of Pennwalt Corporation, Philadelphia, Pa., assignee of the present invention, although copolymers of vinylidene fluoride have been found to work satisfactorily.

The wax retains visible impressions of the relative positions and shapes of the tooth crowns, as well as bite deflection and premature teeth engagement indicia. The wax should deform plastically without affecting the spatial relationship of the teeth, and normally such condition obtains if the carrier sheet thickness is maintained below about 0,025 mm. The stacked piezoelectric film material, on the other hand, permits sliding bite force measurements to be precisely continuously monitored, which measurements may be permanently recorded by conventional means. If the total thickness of both piezoelectric films is greaer than about 0.025 mm, an artificial prematurity may result.

BRIEF DESCRIPTION OF THE DRAWINGS

FIGS. 5, 6, 7, and 8 are diagrammatic illustrations of discriminating bite force indicator strips with dental impression wax omitted for purposes of clarity.

DETAILED DESCRIPTION OF THE INVENTION

Figure 1:
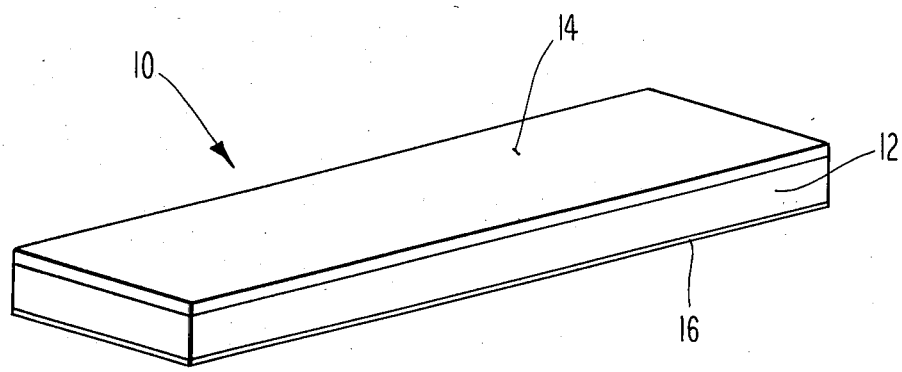
FIG. 1 is a perspective view of one of the metal-coated polymer films having piezoelectric properties used in the indicator of the present invention.

In FIG. 1, piezofilm assembly 10 comprises uniaxially or biaxially oriented polymer film 12, preferably KYNAR ® piezofilm, having conventionally applied suitable metallized coatings 14 and 16, typically aluminum, secured to respective faces thereof. Coating 14 is preferably about 1000 Å thick, or about $0.1\mu$, to thereby provide a surface resistivity of about 0.60 ohms per square or sufficient electromagnetic interference shielding to the piezofilm 12. Coating 16 may be thinner, or only about 300 Å, or about $0.03\mu$, to provide a surface resistivity of about 10 ohms per square. Piezofilm assembly 10 is preferably no greater than about 0.025 mm in thickness to avoid any interference with normal interengagement of the teeth, although thicknesses considerably greater may be used at the expense of accuracy and preciseness. I have found, for piezofilm assembly 10, that thicknesses ranging between about 0.016 to 0.020 mm work satisfactorily.

Figure 2:
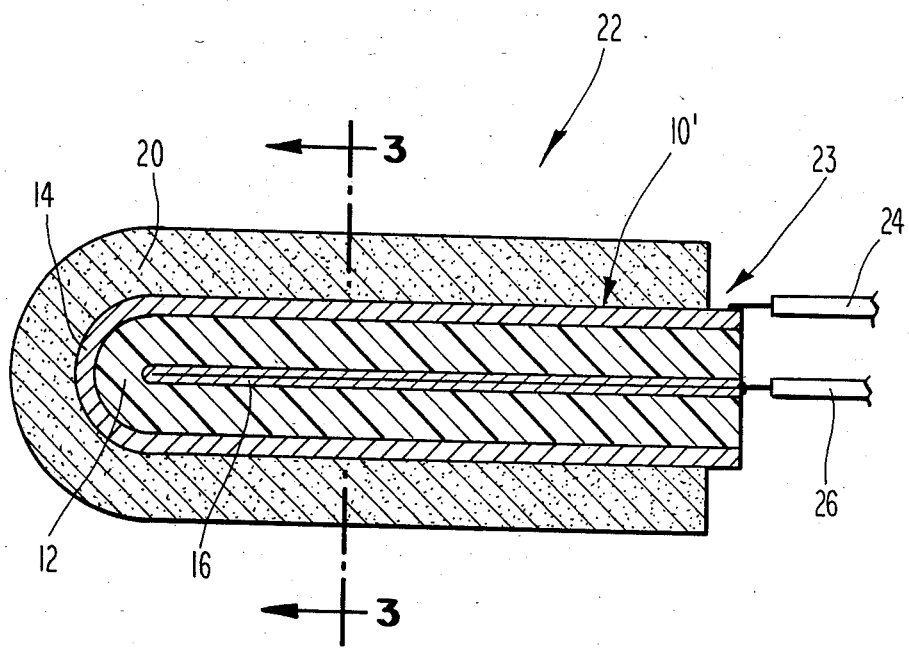
FIG. 2 is a sectional view of the film of FIG. 1 folded in accordance with the teachings of the abovementioned copending patent application to form a transducing element, the folded film being substantially coated with dental impression wax.

Thus, when coated piezofilm assembly 10 is folded, as shown exaggeratedly in FIG. 2, and piezofilm 12 measures $9.0\mu$ thick, while coatings 14 and 16 are are $0.1\mu$ thick and $0.03\mu$ thick respectively, the folded piezofilm assembly 10' will have a total thickness of $18.26\mu$.

The folded piezofilm assembly 10' is provided with a layer of dental bite wax 20. The wax should be less than 0.5 mm thick, and preferably 0.35 mm. Wax 20 overlaps the folded piezofilm assembly 10' on each edge (except at front portion 23) by about ⅛" to form a dental strip or dental impression strip occlusal force indicator 22.

Figure 4:
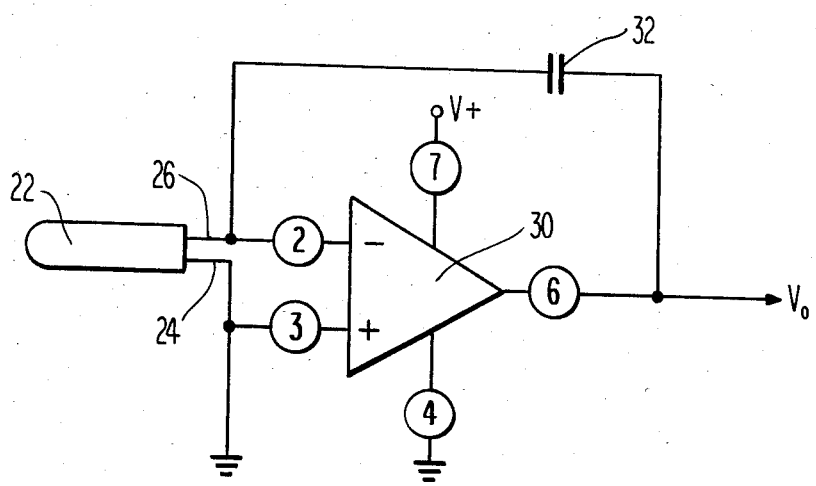
FIG. 4 is a schematic diagram of electronic means for converting voltages generated by the folded high impedance piezofilm of FIG. 2 or stacked superposed piezofilm strips of the present invention to low impedance voltage outputs.

Wire leads from shielded coaxial cables 24 and 26 make contact to the metallized coatings 14 and 16 respectively; the high side 26, which may be + or —, is connected to the negative terminal of an IC operational amplifier 30 while the low side 24 is grounded with the positive terminal of op-amp 30 (FIG. 4).

Op-amp 30 converts the high impedance output from the folded piezofilm assembly 10' to a low impedance voltage output which can be transmitted to a suitable display device (not shown) with no pickup of unwanted signals. The charge generated by folded piezofilm assembly 10' is collected by a feedback capacitor 32 whose voltage is measured as the output voltage of op-amp 30:

$$V_o(t) = \frac{1}{C} Q(t)$$

where $V_o$ = voltage output of op-amp 30
t = time
C = capacitance of capacitor 32
Q = closed circuit charge output of folded piezofilm assembly 10′

The numerals 2, 3, 4, 6 and 7 leading from op-amp 30 merely designate conventional pin connections. Voltage output, $V_o$, is proportional to the time integral of the current output of folded piezofilm assembly 10′ and increases as the force of the bite increases.

Voltage output, $V_o$, may be connected for display on a storage oscilloscope, or to a strip chart recorder if a permanent record of the bite force is desired, and to speaker means where amplitude or pitch may indicate the instantaneous value of the bite force.

Figure 3:
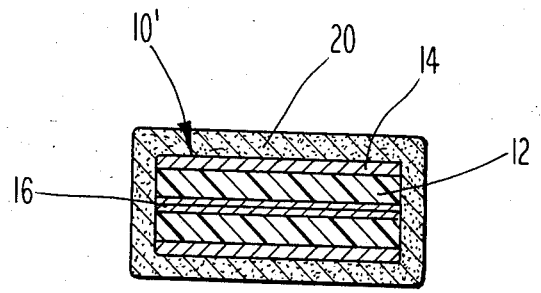
FIG. 3 is a sectional view of FIG. 2 taken along line 3—3 thereof.
Figure 7:
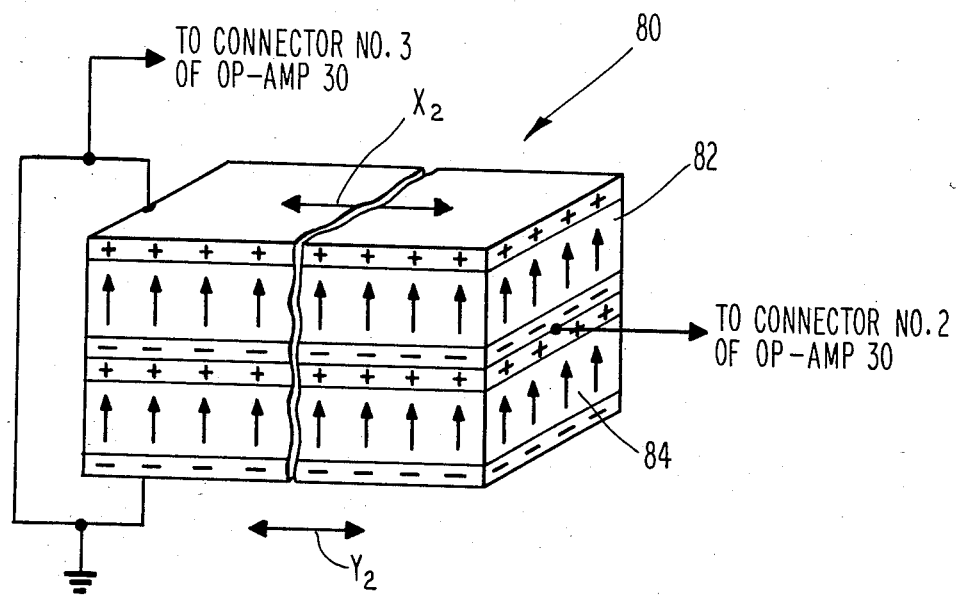
Figure 8:
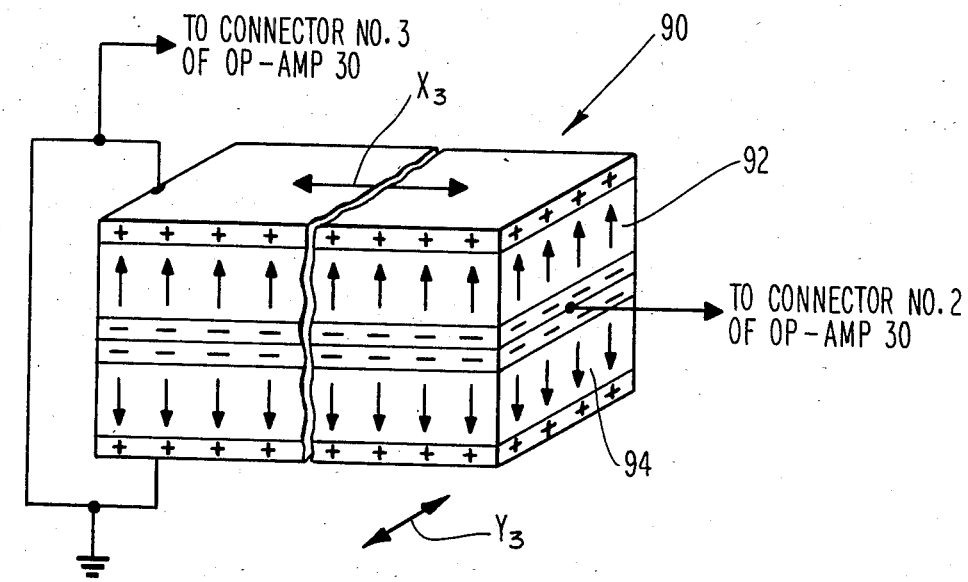

FIGS. 5, 6, 7, and 8 illustrate dental strips for analyzing and monitoring sliding bite forces, rather than pure compression bite forces, although compression bite force data may be obtained from the strips illustrated in FIGS. 6 and 8. It is understood that dental impression wax will be provided over the outermost metallized coatings of the strips of FIGS. 5, 6, 7 and 8, as shown in FIGS. 2 and 3.

In FIG. 5, the sensitivity to sliding bite force is enhanced by securing a pair of piezofilm assemblies 40 and 42 in superposed relationship, to form a stacked piezofilm assembly 43, the crystallites of each piezofilm 44 and 46 thereof respectively being preferably uniaxially oriented and preferentially disposed. Both piezofilms 44 and 46 may conveniently be cut from the same polymer film sheet as piezofilm 12, if uniaxially oriented, and will contain predominantly β form crystallites which offer maximum dipole moment per unit cell to thereby exhibit a large net remanent polarization. The direction of mechanical orientation axes of piezofilms 44 and 46, conventionally achieved by stretching or rolling of the film, is shown by arrows X and Y respectively. Arrow X indicates the direction of mechanical orientation or alignment of the chain axes of crystallites comprising piezofilm 44, which direction parallels its length. By the simple expediency of rotating a piece of the strip of piexofilm (from which piezofilm 46 is cut) about 90° and securing said rotated piezofilm of desired size to piezofilm 44 as shown in FIG. 5, a pair of piezofilms 44 and 46, each having a mechanical orientation axis disposed at right angles to each other is obtained, to form the stacked piezofilm assembly 43.

Crystallites C in piezofilms 44 and 46 are similarly electrically oriented.

The positively charged metallized coating 50 of piezofilm assembly 40 is grounded with the negatively charged metallized coating 52 of piezofilm assembly 42. On the other hand, the negatively charged metallized coating 54 of piezofilm assembly 40 is shorted to the positively charged metallized coating 56 of piezofilm assembly 42. The equal charges of the films are thus effectively cancelled and no voltage differential is developed between ground and the conductor K leading to the No. 2 connector pin of op-amp 30, and hence, an insensitive pure compression bite force indicator results. Sliding bite deflection motion measurements however will be enhanced by the generation of voltages which are not cancelled to thereby provide a voltage differential by the stacked piezofilm assembly 43.

Hence, for sliding bite action rather than pure compressive biting action, piezofilm 40, having a mechanical orientation axis X in a longitudinal or left-right direction, will be more sensitive to sliding bite movements which tend to parallel orientation axis X, whereas piezofilm 46, having a transversely disposed mechanical orientation axis in the Y direction, will be more sensitive to sliding bite movements approaching the Y-axis direction of movement. This follows from the fact that uniaxially oriented piezofilms possess greater sensitivity to stretching in the orientation direction than in a direction normal thereto in the plane of the film.

Voltages thus developed across stacked assembly 43 are effective in discriminating sliding bite forces which may be continuously monitored electronically, as abovediscussed. More specifically, conductor K is connected to the No. 2 connector of op-amp 30 while the grounded coatings are connected to No. 3 connector.

In FIG. 6, the like charged metallic coatings 60 and 62 of piezofilm assemblies 64 and 66 respectively are grounded resulting in a compression sensitive bite force indicator. Sliding bite force indication is also enhanced, i.e., voltages generated by the piezofilm assemblies are greater, especially when the direction of sliding bite force or deflection coincides with the crystallite chain axes $X_1$ and $Y_1$ respectively of piezofilms 68 and 70. Crystallites $C_1$ in piezofilms 68 and 70 are oriented as shown. Both negatively charged metallized coatings 72 and 74 are secured to each other and connected to op-amp 30 via conductor $K_1$ to connector No. 2. Piezofilm assemblies 64 and 66 form stacked piezofilm assembly 75.

Because biting action ideally involves mating of cusps into corresponding grooves or indentations of opposing teeth, a bending action or force is imparted to the piezofilms, causing different portions of each to be stretched and compressed. Thus, in a two film construction utilizing a differential mode, effects are cancelled which strike the two films simultaneously and identically, e.g., heat, EMI radiation, and the like. However, biting action causing a differential voltage to be generated can be monitored and recorded, as abovediscussed.

Differential modes are achieved in the assemblies of FIGS. 5 and 7 as shown, or, in the assemblies of FIGS. 6 and 8 if the two piezofilm assemblies are utilized in the series mode, i.e., one outer metallic coating 60 (FIG. 6, for example) is connected to ground while the other outer metallic coating 62 is connected to the No. 2 connector of op-amp 30 (not shown). Conductor $K_1$ will thus not be needed.

By disposing the directions of mechanical orientation axes $X_1$ and $Y_1$ of FIG. 6, or their aligned crystallite chain axes, at about 45° to the length of the piezofilm assemblies, sliding bite sensitivity indication may be enhanced when sliding bite deflection occurs at an angle of about 45°. Of course, sliding bite force voltage indications which derive from sliding bite forces which deviate from 45° will be progressively diminished as complete left-right or front-to-back sliding movement is approached.

In FIG. 7, stacked piezofilm assembly 80 is identical with stacked piezofilm assembly 43 of FIG. 5 with the exception of the direction of their mechanical orientation axes. Thus, in FIG. 5, the mechanical orientation axes of piezofilm assemblies 44 and 46 are normal to each other whereas the piezofilm assemblies 82 and 84 of FIG. 7 have their mechanical orientation axes $X_2$ and $Y_2$ respectively in parallel relationship.

Stacked assembly 80 is insensitive to compression bite forces but very sensitive to sliding bite forces parallel to the axes of mechanical orientation. If it is known or suspected that the patient is suffering or experiencing front-back type sliding occlusion, then, of course, another stacked assembly having mechanical orientation axes paralleling front-back movement may be employed, or the present assembly rotated up to about 90° within the patient's mouth, care being exercised with the placement of wire leads 24 and 26, or the assembly of FIG. 8 may be used.

FIG. 8 shows a stacked piezofilm assembly 90, identical with stacked piezofilm assembly 75 of FIG. 6, except that mechanical orientation axes $X_3$ and $Y_3$ of piezofilm assemblies 92 and 94 respectively are normal to each other, unlike the parallel disposed axes $X_1$ and $Y_1$ in FIG. 6. The assembly 90 is sensitive to both compression and sliding bite forces.

The present sliding bite force indicator may be used advantageously to monitor the occlusion of teeth other than natural.

For purposes of demonstration, the piezofilm assemblies 43, 75, 80 and 90, may be coated with polytetrafluoroethylene, polyethylene, and the like, which is non-permanently deformable and reusable, in lieu of wax, and will not provide bite impressions, but will indicate to the dentist and patient that continuous monitoring and recording of sliding bite forces exerted during occlusal analyses may readily be effected. The non-permanently deformable and reusable material may be up to several millimeters in thickness and may be coated over the piezofilm assemblies 43, 75, 80 and 90, as is wax 20 (FIGS. 2 and 3) or in any other suitable manner.

Alternative electronic means for monitoring output voltages from the piezofilm assemblies may be utilized.

Bite deflection may be defined as any contact between opposing teeth wherein occlusal surfaces thereof do not make contact in a normal manner. If the contact is accompanied by undesirable sliding therebetween, a sliding bite deflection results, which may be termed longitudinal if sliding substantially coincides with the mechanical orientation axes X, $X_1$, $X_2$ or $X_3$; and transverse, if sliding substantially concides with mechanical orientation axes Y or $Y_3$.

It is understood that the total thickness of piezofilm strips 43, 75, 80 and 90 are approximately 0.020 mm thick, and do not exceed about 0.025 mm. Thus, each uncoated piezofilm may be approximately $9.0\mu$ thick and each outer and inner metallized coatings may be about $0.1\mu$ and $0.03\mu$ respectively for a total stack thickness of approximately $18.26\mu$.

One non-electrically active dental impression strip described in the aforementioned U.S. Pat. No. 3,604,116 may be used simultaneously with a sliding bite force indicator strip of the present invention on opposite sides of the mouth in order to provide non-prejudiced bite monitoring.

I claim:

1. Bite force occlusal indicating device comprising piezopolymer film means having a metallized coating on each face thereof to form a piezoelectric film assembly, said polymer film means including mechanically uniaxially oriented dipole crystallites therein, each of said coatings exhibiting opposite polarity, two of said piezoelectric film assemblies being secured in superposed face-to-face metallized coating contact relationship to form a stacked piezofilm assembly, electrical means connected to said stacked piezofilm assembly for conducting electrical output generated thereby, said output being generated when bite force is applied to said stacked piezofilm assembly, each of said uniaxially oriented polymer film means including a mechanical orientation axis substantially parallel with direction of length of said film means, said film means being disposed in superposed relationship at substantially right angles to each other, said metallized coatings in face-to-face contact relationship being of opposite polarity and remaining coatings being grounded, said dipole crystallites of each polymer film means being similarly electrically oriented, a non-permanently or permanently disposable and reusable material coating in contact with outer faces and edges of said stacked piezofilm assembly, said stacked piezofilm assembly providing an insensitive pure compression bite force indicating device and a sensitive sliding bite force indicating device when said bite force is applied to said non-permanent or permanent material coating of said stacked piezofilm assembly.

2. Device of claim 1 wherein said polymer film means are disposed in superposed parallel relationship to each other to form a first stacked piezofilm assembly, said first stacked piezofilm assembly being insensitive to compression bite forces and sensitive to sliding bite forces exerted parallel to axes of said mechanical orientation of said polymer film means.

3. Bite force occlusal indicating device comprising piezopolymer film means having a metallized coating on each face thereof to form a piezoelectric film assembly, said polymer film means including mechanically uniaxially oriented dipole crystallites therein, each of said coatings exhibiting opposite polarity, two of said piezoelectric film assemblies being secured in superposed face-to-face metallized coating contact relationship to form a stacked piezofilm assembly, electrical means connected to said stacked piezofilm assembly for conducting electrical output generated thereby, said output being generated when bite force is applied to said stacked piezofilm assembly, each of said uniaxially oriented polymer film means including a mechanical orientation axis substantially parallel with direction of length of said film means, said film means being disposed in superposed relationship at substantially right angles to each other, said metallized coatings in face-to-face contact relationship being of like polarity and remaining coatings being grounded, said dipole crystallities of each polymer film means being dissimilarly electrically oriented, a non-permanently or permanently deformable and reusable material coating in contact with outer faces and edges of said stacked piezofilm assembly, said stacked piezofilm assembly providing a sensitive compression bite force indicating device and a sensitive sliding bite force indicating device when said bite force is applied to said non-permanent or permanent material coating of said stacked piezofilm assembly.

* * * * *